United States Patent [19]
Lecouve et al.

[11] Patent Number: 6,133,454
[45] Date of Patent: Oct. 17, 2000

[54] METHOD FOR PREPARING A SUBSTITUTED PERHYDROISOINDOLE

[75] Inventors: Jean-Pierre Lecouve, Le Havre; Claude Fugier, Gruchet le Valasse; Jean-Claude Souvie, Le Havre, all of France

[73] Assignee: Adir et Compagnie, Courbevoie, France

[21] Appl. No.: 09/446,848

[22] PCT Filed: Jul. 1, 1998

[86] PCT No.: PCT/FR98/01405

§ 371 Date: Mar. 20, 2000

§ 102(e) Date: Mar. 20, 2000

[87] PCT Pub. No.: WO99/01430

PCT Pub. Date: Jan. 14, 1999

[30] Foreign Application Priority Data

Jul. 3, 1997 [FR] France .................................... 97 08431

[51] Int. Cl.⁷ ................................................. C07D 209/44
[52] U.S. Cl. ............................................................ 548/515
[58] Field of Search ............................................. 548/515

[56] References Cited

FOREIGN PATENT DOCUMENTS 0507534A 10/1992 European Pat. Off. .

*Primary Examiner*—Laura L. Stockton
*Attorney, Agent, or Firm*—The Firm of Gordon W. Hueschen

[57] ABSTRACT

The present invention relates to a process for the industrial synthesis of a substituted perhydroisoindole of formula (I):

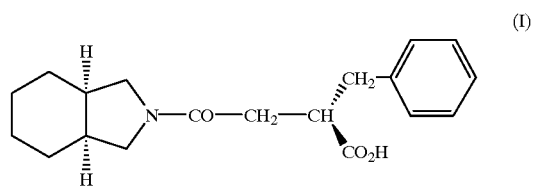

and of pharmaceutically acceptable salts thereof.

The compound of formula (I) and its addition salts have especially valuable pharmacological properties. It is a very powerful secretor of insulin, which makes it useful in the treatment of non-insulin-dependent diabetes.

7 Claims, No Drawings

METHOD FOR PREPARING A SUBSTITUTED PERHYDROISOINDOLE

The present application is a U.S. National Application filed under 35 USC 371 of PCT/FR98/01405, filed Jul. 1, 1998, based upon French Application Serial No. 97.08431, filed Jul. 3, 1997.

The present invention relates to a process for the industrial synthesis of a substituted perhydroisoindole of formula (I):

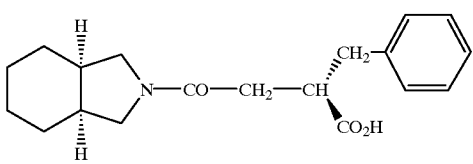

(I)

and of pharmaceutically acceptable salts thereof.

The compound of formula (I) and its addition salts have especially valuable pharmacological properties. It is a very powerful secretor of insulin, which makes it useful in the treatment of non-insulin-dependent diabetes.

The compound of formula (I), its preparation and its use therapeutically have been described in European Patent Specification EP 0 507 534. The industrial preparation of a compound such as the compound of formula (I), however, requires an in-depth investigation of all the reaction steps, of the selection of starting materials, and of the reagents and solvents that make it possible to obtain optimum yields.

The process for the synthesis of the compound of formula (I) described in Patent Specification EP 0 507 534 does not enable the compound to be obtained with an optimum yield. In fact, obtaining the isomer of interest by the synthesis method described does not enable the desired regioselectivity to be obtained. It is thus necessary to carry out a number of purification operations in order to obtain the "pharmaceutical grade" isomer.

Given the pharmaceutical value of the compound and given the absence of a process that enables it to be obtained with a good yield, with satisfactory purity and, if possible, starting from inexpensive starting materials that are commercially available, more in-depth investigation has been carried out and has resulted in the development of a new especially valuable synthesis process.

The invention relates more specifically to a process for the preparation of the compound of formula (I), characterised in that dimethyl succinate is reacted with benzaldehyde in methanolic medium, to yield the diacid of formula (II):

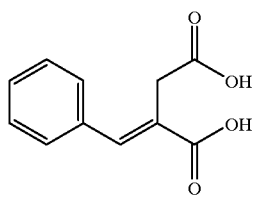

(II)

which, after heating in an aprotic solvent, such as tetrahydrofuran or isopropyl ether, in the presence of acetic anhydride, yields the anhydride of formula (III):

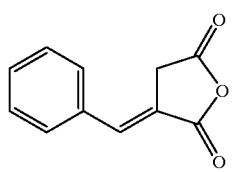

(III)

which is reacted with the perhydroisoindole of formula (IV) in an aprotic solvent, such as toluene, acetonitrile, ethyl acetate, methyl tert-butyl ether or tetrahydrofuran, or in a tetrahydrofuran/toluene mixture,

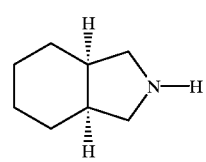

(IV)

to yield the compound of formula (V):

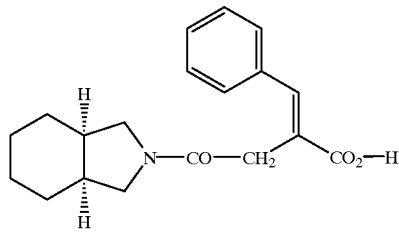

(V)

which is subjected to catalytic hydrogenation using as asymmetric hydrogenation catalyst the complex rhodium/(2S,4S)-N-butoxycarbonyl-4-diphenylphosphino-2-diphenylphosphino-metlhylpyrrolidine or Rh/(S,S) BPPM, in methanolic or methylene chloride medium, followed by conversion to a salt in the presence of an amine A to yield a compound of formula (VI):

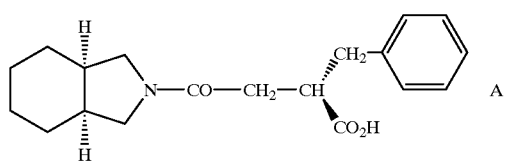

(VI)

which
in a basic medium in the presence of a mineral salt yields an addition salt of the compound of formula (I), which is converted, if desired, into the corresponding acid, or,
in an acidic medium yields the compound of formula (I), which is converted, if desired, into a pharmaceutically acceptable addition salt.

Amongst the pharmaceutically acceptable addition salts, there may be mentioned by way of non-limiting example the sodium and calcium salts in hydrated or non-hydrated form.

The preferred addition salt is the calcium salt.

The process is especially valuable for the following reasons:

The opening up of the anhydride of formula (III) by the perhydroisoindole of formula (IV) allows very great regioselectivity to be obtained. In fact, the compound of formula (V) is isolated with a regioselectivity of more than 99.5%.

The enantioselective reduction of the compound of formula (V) by the complex Rh/(S,S)BPPM provides an enantiomeric excess of more than 92%. The molar ratio of complex/substrate used in this Step is from 1/2000 to 1/10000 and preferably from 1/2000 to 1/4000.

The rhodium complex Rh/(S,S)BPPM is known from the literature to be an enantiospecific hydrogenation catalyst.

However, in methanol or methylene chloride (reaction solvents), the acid of formula (I/a) has a tendency to evolve to a mixture of regioisomers (I/a)/(I/b):

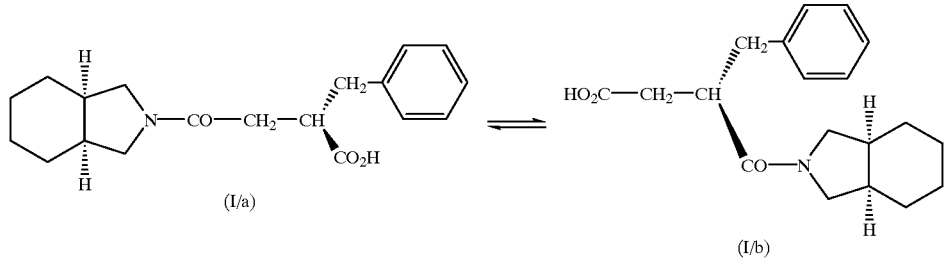

A kinetic study has made it possible to show that the percentage of regoisomer (I/b) increases rapidly as a function of the time and temperature. It has been shown that when compound (I) is in the presence of an amine A, the formation of the compound of formula (I/b) is slowed down considerably.

By way of example, at 65° C. after 12 hours in solution in methanol, the percentage of compound (I/b) is approximately 9% when the compound is in the form of the free acid, whilst the percentage of compound (I/b) is approximately 1% when the compound is in the to form of a salt of an amine A. That constitutes a considerable advantage in the development of this industrial process.

Also, the crystallisation of the resulting salt is readily applicable on an industrial scale and enables excellent enantiomeric and chemical purification of the expected product. It also enables all traces of catalyst to be eliminated.

Amongst the amines A that can be used in this Step of the reaction, there may be mentioned (R)-1-phenylethylamine, morpholine, N-methylmorpholine and cyclohexylamine. The preferred amines are (R)-1-phenylethylamine and morpholine.

The following Examples illustrate the invention but do not limit it in any way.

EXAMPLE 1

Calcium bis-2-(S)-benzyl-4-oxo-4-(cis-perhydroisoindol-2-yl)butyrate dihydrate

Step A: Benzylidenesuccinic Acid 700 mmol of dimethyl succinate and then 20 ml of methanol are added to 290 mmol of sodium methylate dissolved in 80 ml of methanol. The mixture is brought to reflux, and 236 mmol of benzaldehyde are slowly added, followed by 20 ml of methanol. The mixture is maintained at reflux, with stirring, for one hour, and then 100 ml of methanol are distilled off. 120 ml of water and 120 ml of 10N sodium hydroxide solution are added to the concentrated reaction mixture. The removal of the methanol by distillation is continued. The residue is diluted with 150 ml of water. After the addition of dichloromethane, the diacid is precipitated by the slow addition of 12N hydrochloric acid. The diacid is filtered and washed with dicliloromethane and then with water. Drying yields the expected product.

Melting point: 199° C.

Step B: Benzylidenesuccinic Anhydride 291 mmol of the compound obtained in the preceding Step are suspended in 180 ml of isopropyl ether. 320 mmol of acetic anhydride are added and the suspension is refluxed for 3h 30. Cooling to 4° C., filtration of the resulting anhydride and washing with isopropyl ether yield the expected product.

Melting point: 168° C.

Step C: 2-[(Cis-perhydroisoindol-2-yl)carbonylmethyl]-3-phenylacrylic Acid

A solution of 175 mmol of perhydroisoindoline in 32 ml of toluene is added very slowly to 167 mmol of the anhydride obtained in the preceding Step suspended in 250 ml of toluene. The mixture is cooled to −5° C. The resulting monoamide precipitate is filtered off and washed with ice-cold toluene. Drying yields the expected product.

Melting point: 162° C.

Step D: 1-(R)-Phenylethylamine 2-(S)-benzyl-4-oxo-4-(cis-perhydroisoindol-2-yl)-butyrate 80 mmol of the amide obtained in the preceding Step are dissolved in 75 ml of methanol. 40 micromoles of (S,S) BPPM are dissolved in 15 ml of methanol, and 20 micromoles of [Rh(COD)Cl]$_2$ are dissolved in 15 ml of methanol. The solutions are degassed, placed in the hydrogenation reactor and hydrogenated at 20° C. under 5 bars. 250 ml of toluene and, at 5° C., a solution of 82.5 mmol of (R)-1-phenylethylamine in 100 ml of toluene are added to the metlhanolic hydrogenation solution. The methanol is expelled under reduced pressure at ambient temperature, and 300 ml of toluene are added. The resulting precipitate is filtered off at 20° C. and washed twice with 20 ml of toluene each time. After drying, the resulting crude salt is recrystallised from acetone, filtered off and dried to yield the expected product.

Melting point: 144° C.

Step E: Calcium bis-2-(S)-benzyl-4-oxo-4-(cis-perhydroisoindol-2-yl)butyrate Dihydrate 13 ml of an aqueous solution containing 9 mmol of calcium chloride dihydrate are added to 9 mmol of the above-purified 1-(R)-phenylethylamine salt dissolved in 80 ml of an aqueous 1.8% ammonia solution. The resulting precipitate is filtered off, washed with water and dried to yield the expected product.

Melting point: 214° C. $[\alpha]_{365}^{20}$=+32.4 (c=5%, MeOH)

EXAMPLE 2

Calcium bis-2-(S)-benzyl-4-oxo-4-(cis-perhydroisoindol-2-yl)butyrate dihydrate Step A, B and C: These Steps are Identical to Steps A, B and C of Example 1.

Step D: Morpholine 2-(S)-benyl-4-oxo-4-(cis-perhydroisoindol-2-yl)-butyrate

In The hydrogenation is carried out as above. 69 g of morpholine are added to the ice-cold methanolic hydrogenation solution, and concentration is carried out in vacuo at a temperature of less than 25° C. to remove the methanol. The concentrate is adjusted to a weight of 115 g by adding morpholine, and then 250 ml of methyl teri-butyl ether are added and the mixture is stirred at ambient temperature for 20 hours.

The amine salt that precipitates is filtered off and washed with a methyl tert-butyl ether/morpholine mixture and then with methyl tert-butyl ether. Drying yields the expected product.

Melting point: 110° C.

Step E: Calcium bis-2-(S)-benzyl-4-oxo-4-(cis-perhydroisoindol-2-yl)butyrate Dihydrate 25 ml of 1N sodium hydroxide solution and then 28 ml of an aqueous solution containing 12.5 mmol of calcium chloride dihydrate are added to 25 mmol of the above-purified morpholine salt dissolved in 75 ml of ethanol and 30 ml of water. The resulting precipitate is filtered off, washed and dried to yield the expected product. Melting point: 214° C. $[\alpha]_{365}^{20}=+32.4$ (c=5%, MeOH)

What is claimed is:

1. A process for the industrial preparation of a substituted perhydroisoindole of formula (I):

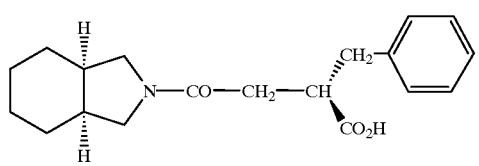

(I)

or a pharmaceutically- acceptable salt thereof, characterised in that dimethyl succinate is reacted with benzaldehyde in methanolic medium, to yield the diacid of formula (II):

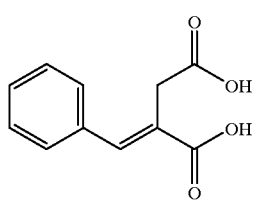

(II)

which, after heating in an aprotic medium in the presence of acetic anhydride, yields the anhydride of formula (III):

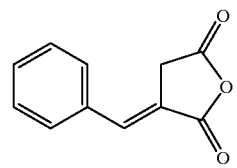

(III)

which is reacted with the perhydroisoindole of formula (IV) in an aprotic solvent

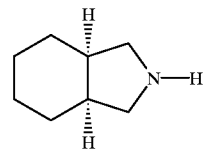

(IV)

to yield the compound of formula (V):

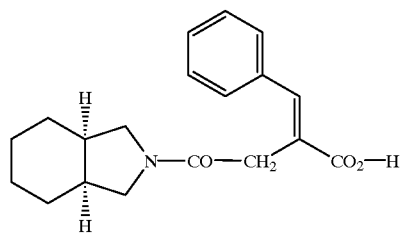

(V)

which is subjected to catalytic hydrogenation using as asymmetric hydrogenation catalyst the complex rhodium/(2S,4S)-N-butoxycarbonyl-4-diphenylphosphino-2-diphenylphosphino-methylpyrrolidine or Rh/(S,S) BPPM, in methanolic or methylene chloride medium, followed by conversion to a salt in the presence of an amine A selected from the group consisting of (R)-1-phenylethylamine, morpholine, N-methylmorpholine and cyclohexylamnine, to yield a compound of formula (VI):

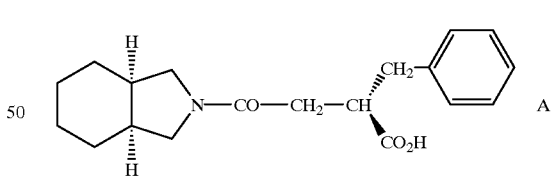

(VI)

which:
in a basic medium in the presence of a mineral salt yields an addition salt of the compound of formula (I), which is converted, if desired, into the corresponding acid, or,
in an acidic medium yields the compound of formula (I), which is converted, if desired, into a pharmaceutically-acceptable addition salt.

2. The process according to claim 1, wherein the amine A used is (R)-1-phenylethylamine.

3. The process according to claim 1, wherein the amine A is morpholine.

4. The process according to claim 1, wherein the amine A is N-methylmorpholine.

5. The process according to claim 1, wherein the amine A is cyclohexylamine.

6. The process according to claim 1 for the preparation of the calcium salt of bis-2-(S)-benzyl-4-oxo-4-(cis-perhydroisoindol-2-yl)butyric acid.

7. The process according to claim 1 for the preparation of calcium bis-2-(S)-benzyl-4-oxo-4-(cis-perhydroisoindol-2-yl) butyrate dihydrate.

* * * * *

UNITED STATES PATENT AND TRADEMARK OFFICE
CERTIFICATE OF CORRECTION

PATENT NO. : 6,133,454
DATED : October 17, 2000
INVENTOR(S) : J-P. Lecouve, C. Fuguer, J-C. Souvie It is certified that error appears in the above-identified patent and that said Letters Patent is hereby corrected as shown below:

Column 3, line 15: "regloisomers" should read:
-- regioisomers --. Page 3, line 21

Column 3, line 31: "regoisomer" should read:
-- regioisomer --. Page 4, line 1

Column 3, line 40: "is in the to form" should read:
-- is in the form --. Page 4, line 7

Column 4, line 5: 'dicliloromethane" should read:
-- dichloromethane --. Page 4, line 29

Column 5, line 6: "Step" should read: -- Steps --.
Page 6, line 8

Column 5, line 9: "2-(S)-benyl-" should read:
-- 2-(S)-benzyl- --. Page 6, line 9

Column 5, line 12: At the beginning of the line,
delete the word "In". Page 6, line 10

UNITED STATES PATENT AND TRADEMARK OFFICE
CERTIFICATE OF CORRECTION

PATENT NO. : 6,133,454
DATED : October 17, 2000
INVENTOR(S) : J.P. Lecouve, C. Fuguer, J-C. Souvie It is certified that error appears in the above-identified patent and that said Letters Patent is hereby corrected as shown below:

```
Column 6, line 43: "cyclohexylamnine," should read:
    -- cyclohexylamine --. Examiner's Amendment,
    page 3, Claim 1, line 17.
```

Signed and Sealed this

Eighth Day of May, 2001

Attest:

NICHOLAS P. GODICI

Attesting Officer     Acting Director of the United States Patent and Trademark Office